United States Patent [19]

Huang

[11] Patent Number: 5,540,416
[45] Date of Patent: Jul. 30, 1996

[54] INJECTION NEEDLE MELTING/DESTROYING DEVICE

[76] Inventor: Chao-Chih Huang, 7F-1, No. 492, Sec. 1, Wan Sou Rd., Kuei Shen Hsiang, T'ao-Yuan Hsien, Taiwan

[21] Appl. No.: 424,652

[22] Filed: Apr. 19, 1995

[51] Int. Cl.[6] .................................................. F23G 5/00
[52] U.S. Cl. .............................. 266/200; 110/250; 219/68
[58] Field of Search ...................................... 266/200, 287; 219/68; 110/250; 128/919; 83/16

[56] References Cited

U.S. PATENT DOCUMENTS

| | | | |
|---|---|---|---|
| 4,965,426 | 10/1990 | Colombo | 219/68 |
| 5,076,178 | 12/1991 | Kohl et al. | 110/250 |
| 5,091,621 | 2/1992 | Butler | 219/68 |
| 5,166,488 | 11/1992 | Peppard | 219/68 |
| 5,212,362 | 5/1993 | Burden et al. | 219/69.1 |
| 5,245,935 | 9/1993 | Fukuda | 110/250 |

*Primary Examiner*—Scott Kastler
*Attorney, Agent, or Firm*—Bacon & Thomas

[57] ABSTRACT

An injection needle melting/destroying device comprising an A(D)C power supply, a power indicator lamp, a transformer having output terminals, two opposite metal plates disposed beside the output terminals of the transformer to define a socket, a collection box disposed under the metal plates and a brush disposed above the metal plates. An injection needle is adapted to be inserted into the socket to make a short circuit so as to produce great current for melting the injection needle. The brush serves to cover the socket and prevent spark from splashing outside the socket during the melting operation.

3 Claims, 6 Drawing Sheets

INJECTION NEEDLE MELTING/DESTROYING DEVICE

BACKGROUND OF THE INVENTION

The present invention relates to an injection needle melting/destroying device, and more particularly to a device which melts and completely destroys used injection needle by means of short circuit current so as to avoid re-use of the injection needle.

FIGS. 1 and 2 show a conventional device for melting used injection needle by current. Such conventional device mainly includes a housing 1 and a control box 3. The housing 2 encloses a pair of freely rotatable shaft members 22, 23 which are parallel to each other. On one side of each shaft member is fixedly disposed multiple groups of opposite and spaced negative and positive electrodes 221, 231 defining a downward tapered socket for an injection needle to insert thereinto. When used, the syringe 1 is inserted and fixed in an entrance 21 of the housing 2 and then a power switch 31 is switched on and an operation switch 32 is pressed so as to supply pulse current to a coil 24 for driving the shaft members 22, 23. At this time, the lowest pair of electrodes 221, 231 will abut against a lower portion of the injection needle 11 of the syringe 1 and make a short circuit between the electrodes 221, 231 and thus produce spark so as to melt and cut apart the lower portion of the injection needle 11. Once the needle is cut apart, an upward pair of electrodes 221, 231 will subsequentially abut against the needle 11. Similar procedures will be performed in sequence to cut apart the needle 11 section by section from the tip portion to a root portion thereof.

According to the above arrangements, several shortcomings exist as follows:

1. With the above design, the danger of current overload cannot be eliminated.
2. Too many electrodes are used in such design and thus the cost therefor is relatively high.
3. No collection means for collecting the molten and broken needle is provided in the conventional device.
4. After molten, a ball-like condensed solid will be formed at the tip of the needle according to the metal properties. Such condensed solid cannot be removed and may block the entrance 21.

Therefore, it is necessary to provide an improved device for melting/destroying used injection needle to solve the above problems.

SUMMARY OF THE INVENTION

It is therefore a primary object of the present invention to provide a device which is able to effectively melt/destroy the used injection needle.

It is a further object of the present invention to provide the above device which is equipped with a fuse means and a monitoring means so as to avoid current overload due to short circuit.

It is still a further object of the present invention to provide the above device which includes a collection box for collecting the molten and broken needles.

It is still a further object of the present invention to provide the above device which employs metal plates as the electrodes, which are surface-treated to diminish the oxidation thereof.

According to the above objects, the injection needle melting/destroying device of the present invention comprises an A(D)C power supply, a power indicator lamp, a transformer having output terminals, two opposite metal plates disposed beside the output terminals of the transformer to define a socket, a collection box disposed under the metal plates and a brush disposed above the metal plates. In addition, a current monitoring means can be disposed for monitoring the value of the current.

The present invention can be best understood through the following description and accompanying drawing, wherein:

DETAILED DESCRIPTION OF THE PREFERRED EMBODIMENT

Figure 1:
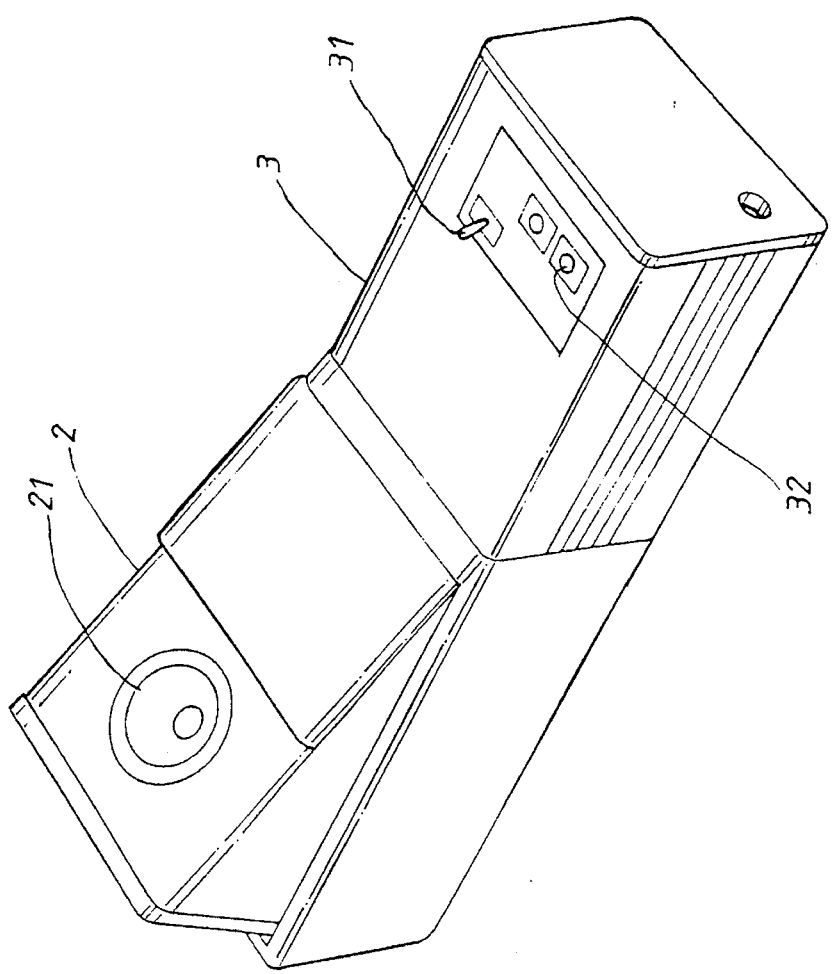
FIG. 1 is a perspective view of a conventional device for melting used injection needle.
Figure 2:
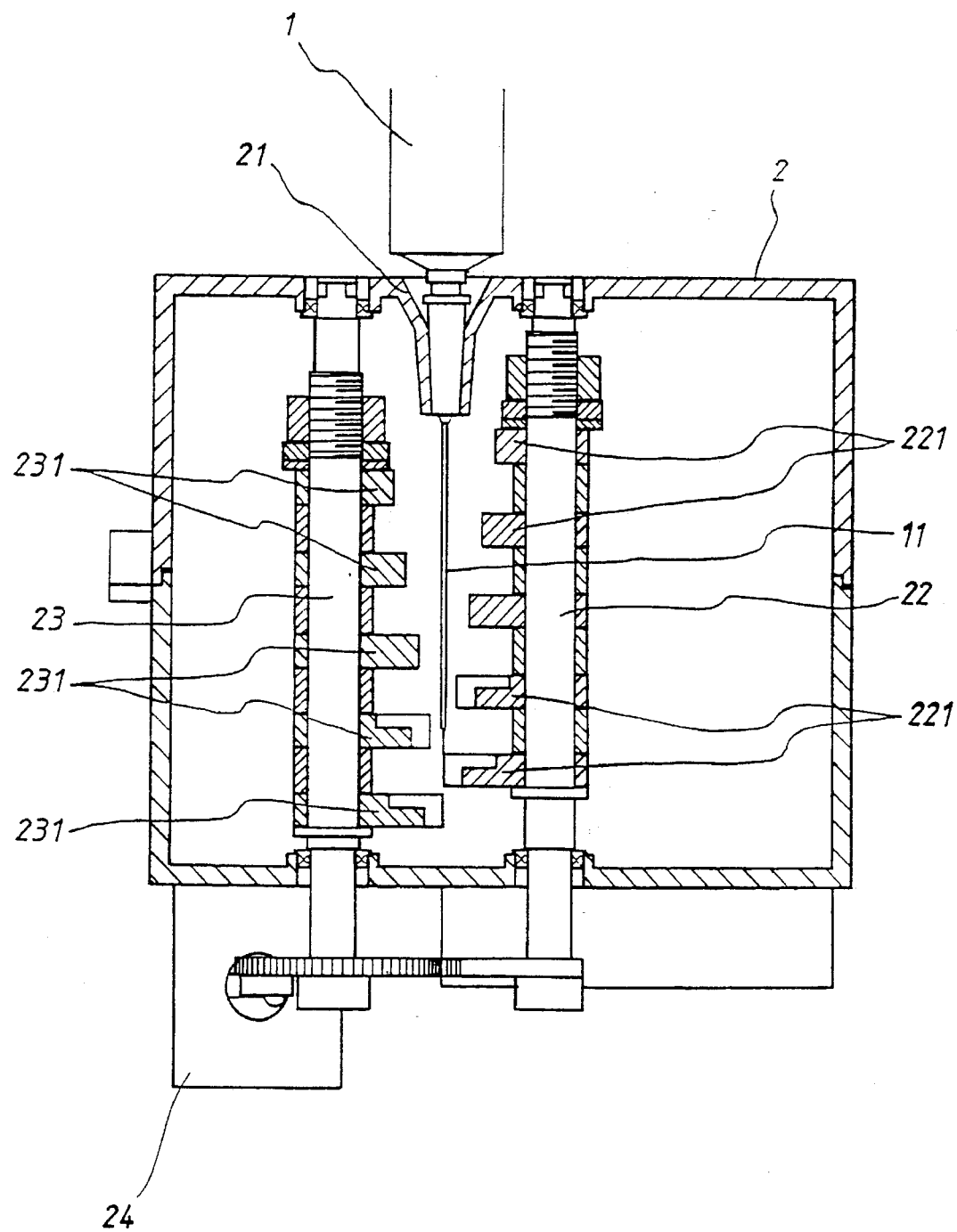
FIG. 2 is a sectional view of the conventional device of FIG. 1, showing the internal structure thereof.
Figure 3:
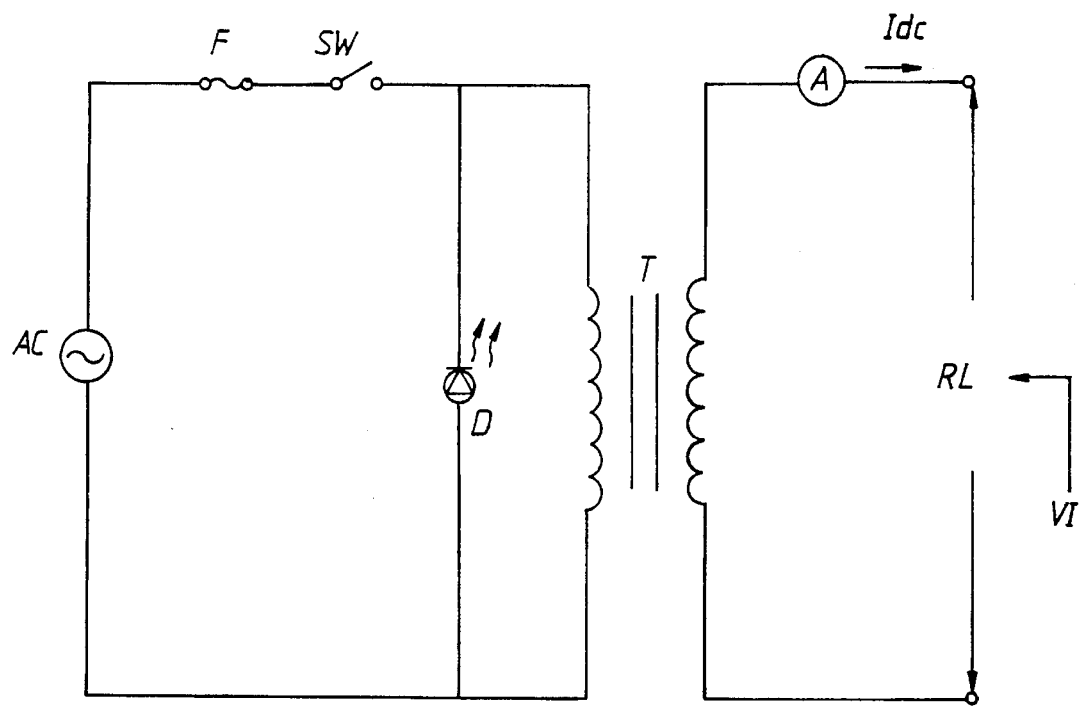
FIG. 3 is a circuit diagram of the present invention.

Please refer to FIG. 3. The injection needle melting/destroying device of the present invention mainly includes an A(D)C power supply AC, a fuse means F, a power switch SW, a power indicator lamp D, an energizing transformer T, a current display (not inevitable element in this invention) and transformer output terminals X1, X2. The load RL of the circuit is produced by inserting an injection needle into the device to make a short circuit between the output terminals X1, X2 as indicated by arrow Vi in FIG. 3.

Referring to FIG. 3, the A(D)C power supply AC serves to supply A(D)C power for melting the metal injection needle, whereby the metal needle M as the load RL can be molten by the great short circuit current. In addition, by means of the added rectifier and accessory circuits thereof, the present device is suitable for both AC and DC power. Therefore, the present device can be widely applied in various situations such as the AC power supply of a therapeutic room or other indoor sites, the DC power supply of an ambulance, a bleeding or therapeutic vehicle or aircraft or other suitable sites, etc. The rectifier and the rectifying circuits are added between the switch SW and the parallelly connected indicator lamp D. This circuit design has been widely used. Therefore, the embodiment of the present invention only refers to the injection needle melting/destroying device utilizing AC power and the rectifying the AC power to the DC power will not be further described hereinafter.

The respective elements connected to two terminals of the AC power supply are provided with AC power for working. However, the great short circuit current for melting the used injection needle M may cause an instantaneous current overload. In order to avoid this, the fuse means F is connected to one terminal of the AC power supply so as to prevent the AC power supply from being burned down due to reverse energization of the overload current and further avoid power cut of the injection needle melting/destroying device. The maximum value of the fuse means should not exceed the maximum output current value of the energizing transformer T so as to effectively avoid the burning down of the power supply by the overload current.

The power switch SW connected after the fuse means F as shown in FIG. 3 mainly serves to avoid the idle consumption of power (the power indicator lamp D, energizing transformer T and current display all will consume power when the circuit is made) before the load RL is added, that is, before the injection needle M is inserted into the device to make the short circuit, so that the power loss of the system caused by the idle consumption branch can be eliminated. Moreover, when necessary, the working power can be cut off at service or cleaning point. The power indicator lamp D is connected after the fuse means F, serving to indicate whether the circuit is working. Therefore, at least a user is able to know whether the circuit before the energizing transformer T is normal. The energizing transformer T is parallelly connected on right side of the power indicator lamp D, serving to boost (or reduce) the DC power to an effective melting current value, whereby when the load RL is added, the current value Idc of the energized terminal is able to melt the needle. The melting current value Idc is determined by the melting point of the load RL, that is, the material, dimension and other features of the metal needle. Generally, the current value should be set according to the maximum syringe commercially available. A current display can be auxiliarily disposed for monitoring the melting current value Idc. Therefore, the user can easily recognize the value of the power consumption and whether a circuit is made between the output terminals X1, X2. However, the current display is not inevitable. For a skilled user, it is not difficult to judge the working state by observing whether the load RL is molten and whether the power indicator lamp D is turned on.

Figure 4:
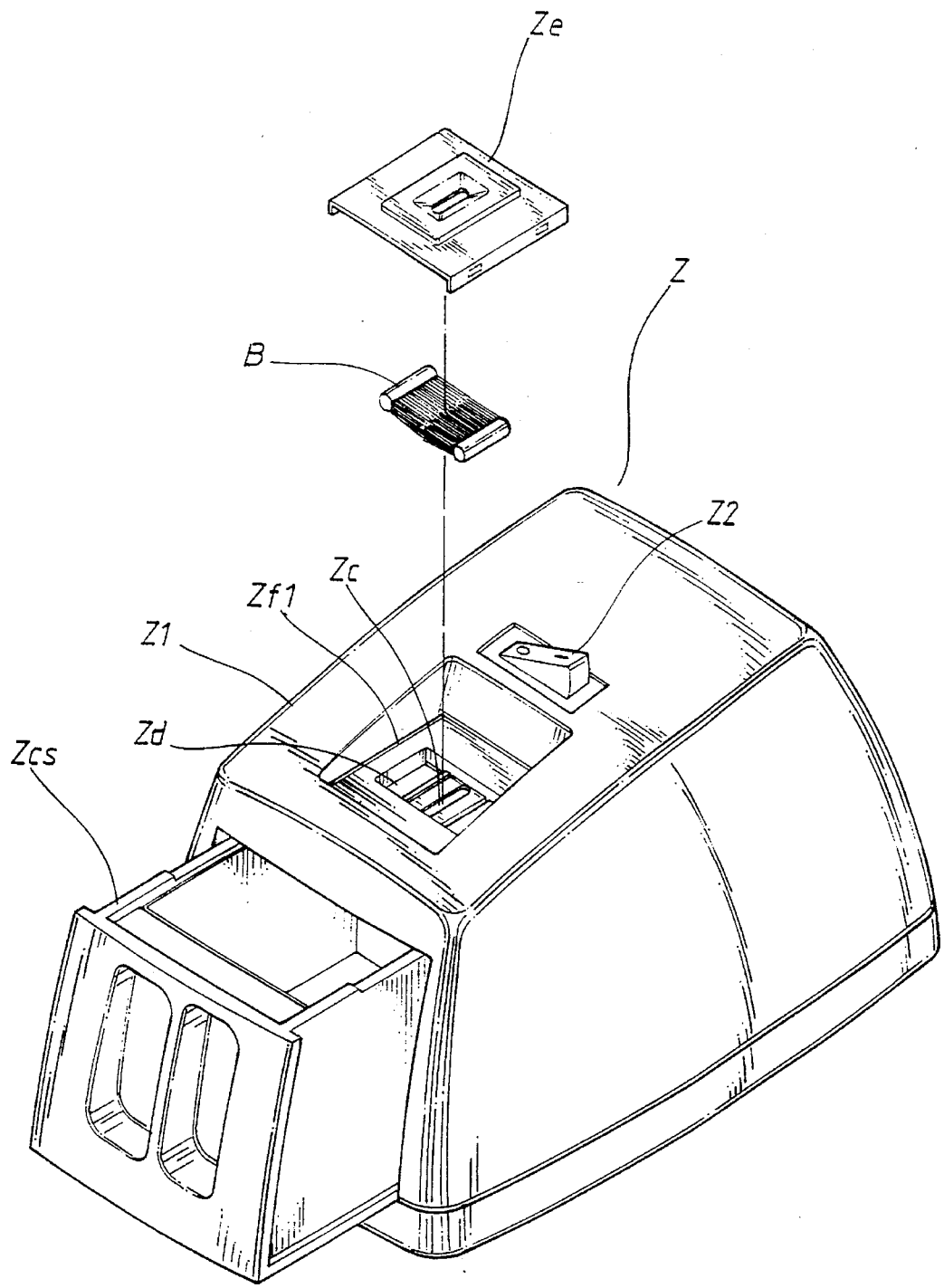
FIG. 4 is a perspective view of the present invention.
Figure 5:
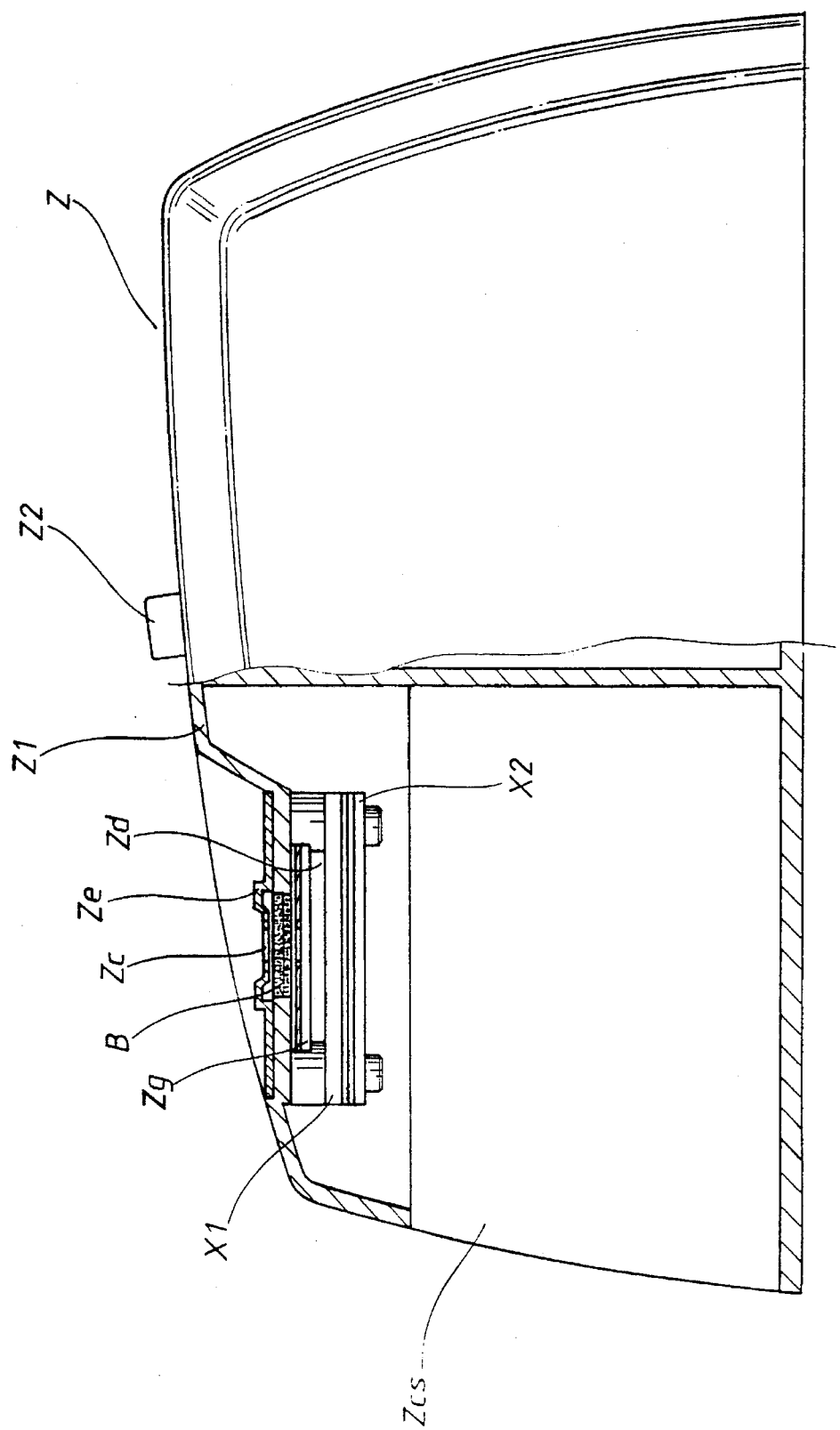
FIG. 5 is a sectional view of the present invention according to FIG. 4.

According to the above arrangements, please further refer to FIGS. 4 and 5, wherein the needle melting/destroying device Z includes a housing Z1, a power switch Z2 (linked with the aforesaid power switch SW), a socket Zc for inserting the injection needle M thereinto, a receptacle Zd for locating a brush B therein, two slits Zf1, Zf2 for locating a cover plate Ze therein and a movable collection box Zcs for receiving the molten needles. In FIG. 5, it is seen that under the socket Zc are sequentially disposed an isolating plate Zg and two output electrodes X1, X2 consisting of metal conductive plates and wires (arranged on two sides of the socket Zc with the conductive plates designed with hook ends to define an inclined socket, so that the injection needle M contacts with the electrodes in a substantially cross pattern) and the power control circuit. Under the electrodes X1, X2 are disposed the collection box Zcs.

Figure 6A:
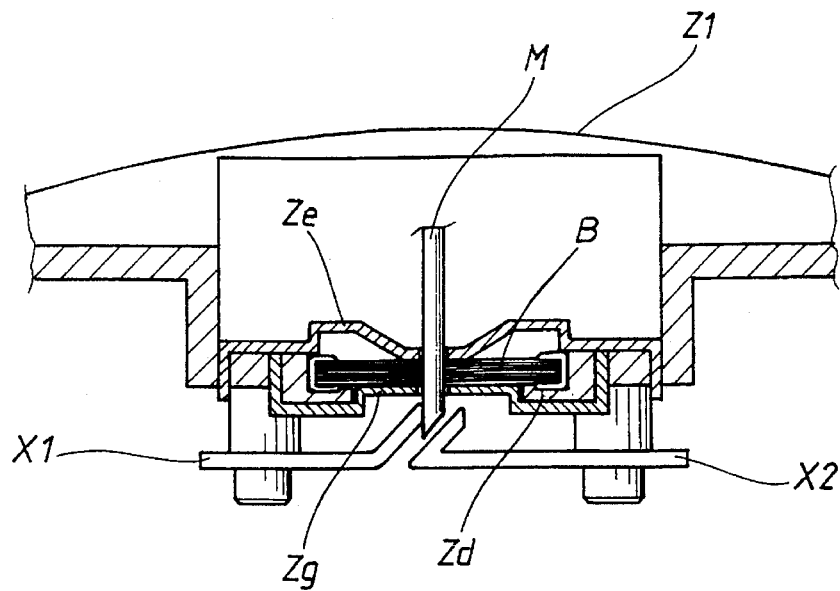
FIG. 6A is a sectional view showing that the injection needle is inserted into the socket of the present invention and not molten yet.
Figure 6B:
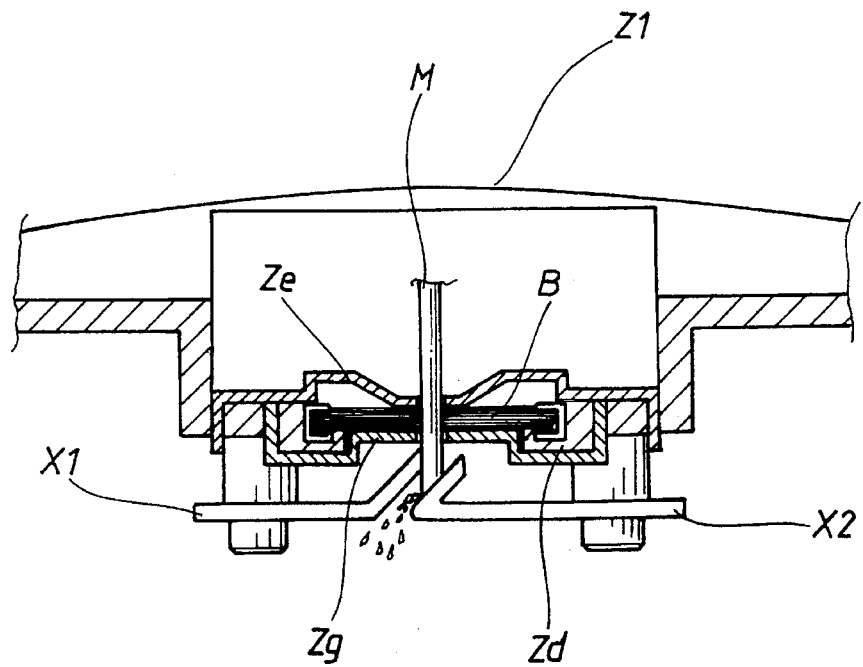
FIG. 6B is a sectional view according to FIG. 6A, showing that the injection needle is molten.

By means of the above design, the user can easily use the melting/destroying device. Referring to FIG. 6A, after the user inserts the needle into the socket Zc, the needle contacts with both the electrodes X1, X2 to make the circuit (referring back to FIG. 3). Because the impedance of the injection needle is very small (and is almost negligible in comparison with large current), after the circuit is made, the current Idc will instantaneously pass between the two terminals of the energizing transformer T to make a substantially short circuit. By means of the short circuit effect, the metal needle in FIG. 6A will be molten into a state as shown in FIG. 6B and the molten metal will drop down into the collection box Zcs. The collected molten metal is then taken out and processed. After the melting of the injection needle is completed, the syringe and the remaining needle are drawn away from the socket Zc for further processing. At the same time, the remaining tip of the metal needle is shaped as a deformed condensed solid. In order to prevent the deformed condensed solid from obstacling the access of the socket, the hard brush B is disposed above the electrodes X1, X2 to brush down the solid before it completely condenses. Therefore, the socket is prevented from being blocked by the solid. Moreover, when the metal needle is molten, the brush B covers the socket Zc so as to prevent the spark of short circuit from splashing outside the device.

It is to be understood that the above description and drawings are only used for illustrating one embodiment of the present invention, not intended to limit the scope thereof. Any variation and derivation from the above description and drawings should be included in the scope of the present invention.

What is claimed is:

1. An injection needle melting/destroying device comprising a housing, a power switch, a socket for inserting an injection needle thereinto, a brush located above and on two sides of said socket, a cover plate for covering said brush and a movable collection box for receiving molten metal of the needle, under said socket being sequentially disposed an isolating plat and two electrodes consisting of metal conductive plates and wires and arranged on two sides of said socket, said collection box being disposed under said electrodes, a power supply circuit controling mechanism being disposed in said housing under said socket, said power supply circuit controlling mechanism including an A(D)C power supply, a fuse means, a power switch, a power indicator lamp, an energizing transformer having output terminals connected to said electrodes, whereby the metal injection needle is adapted to be inserted into said socket to make a short circuit so as to produce a short circuit current for melting and destroying the needle, said brush serving to brush away condensed solid remaining on a tip of the needle and prevent sparks from splashing outside said device due to short circuit current.

2. A device as claimed in claim 1, wherein a current display is connected to said electrodes in series for monitoring a value of the short circuit current.

3. A device as claimed in claim 1, wherein a bridge rectifier is connected between said power switch and said power indicator lamp for rectifying AC power into DC power.

* * * * *